United States Patent
Hennek et al.

(10) Patent No.: US 11,279,968 B2
(45) Date of Patent: Mar. 22, 2022

(54) DNA-ANTIGEN EXCHANGE AND AMPLIFICATION

(71) Applicant: Ultivue, Inc., Cambridge, MA (US)

(72) Inventors: Stephanie Rae Hennek, Medford, MA (US); Mael Manesse, Medford, MA (US)

(73) Assignee: Ultivue, Inc., Cambridge, MA (US)

(*) Notice: Subject to any disclaimer, the term of this patent is extended or adjusted under 35 U.S.C. 154(b) by 202 days.

(21) Appl. No.: 16/273,581

(22) Filed: Feb. 12, 2019

(65) Prior Publication Data
US 2019/0177767 A1 Jun. 13, 2019

Related U.S. Application Data

(62) Division of application No. 15/941,770, filed on Mar. 30, 2018, now Pat. No. 10,246,738.
(Continued)

(51) Int. Cl.
*C12Q 1/682* (2018.01)
*C12Q 1/6804* (2018.01)
(Continued)

(52) U.S. Cl.
CPC .......... *C12Q 1/682* (2013.01); *C12Q 1/6804* (2013.01); *C12Q 1/6844* (2013.01);
(Continued)

(58) Field of Classification Search
CPC .... C12Q 1/682; C12Q 1/6804; C12Q 1/6844; C12Q 2531/125; G01N 2458/10; G01N 33/5308; G01N 33/582
See application file for complete search history.

(56) References Cited

U.S. PATENT DOCUMENTS 6,344,329 B1  2/2002  Lizardi
6,511,809 B2  1/2003  Baez et al.
(Continued)

FOREIGN PATENT DOCUMENTS

EP  868530 A1  10/1998
EP  1915466 B1  11/2010
(Continued)

OTHER PUBLICATIONS

Abe et al., "Affinity labeling of vertebrate oxidosqualene cyclass with a tritiated suicide substrate," Biochemical and Biophysical Research Communications, 187(1):32-33, Aug. 31, 1992.
(Continued)

*Primary Examiner* — Young J Kim
(74) *Attorney, Agent, or Firm* — McNeill Baur PLLC

(57) ABSTRACT

Methods for imaging are described, including, but not limited to a method comprising: (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with antigen-bound imager strands and antigen-specific binding partners linked (directly or indirectly) to optical labels, wherein the antigen-bound imager strands have complementarity to a docking strand, directly or indirectly, and wherein each antigen-specific binding partner is linked to one or more optical labels, and wherein antigen-specific binding partners of different specificity are linked to distinct optical labels, (4) optionally removing unbound antigen-bound imager strands and/or antigen-specific binding partners, (5) imaging the sample to detect bound labeled antigen-specific binding partners, (6)
(Continued)

optionally removing/extinguishing signal from the optical labels, and (7) optionally repeating steps (1)-(6), or any subset thereof.

20 Claims, 6 Drawing Sheets

Related U.S. Application Data

(60) Provisional application No. 62/479,676, filed on Mar. 31, 2017.

(51) Int. Cl.
*G01N 33/58* (2006.01)
*C12Q 1/6844* (2018.01)
*G01N 33/53* (2006.01)

(52) U.S. Cl.
CPC ....... *G01N 33/5308* (2013.01); *G01N 33/582* (2013.01); *G01N 2458/10* (2013.01)

(56) References Cited

U.S. PATENT DOCUMENTS

| | | | |
|---|---|---|---|
| 6,531,286 B2 | 3/2003 | Jayasena et al. | |
| 6,797,474 B2 | 9/2004 | Lizardi | |
| 7,422,855 B2 | 9/2008 | DiCesare | |
| 7,553,619 B2 | 6/2009 | Kumar et al. | |
| 7,604,981 B1 | 10/2009 | Harris et al. | |
| 7,618,776 B2 | 11/2009 | Lizardi | |
| 7,767,414 B1 | 8/2010 | Smith et al. | |
| 7,883,669 B2 | 2/2011 | Sun et al. | |
| 8,043,834 B2 | 10/2011 | Abarzúa et al. | |
| 9,008,378 B2 | 4/2015 | Micheva et al. | |
| 9,578,306 B2 | 2/2017 | Micheva et al. | |
| 9,625,387 B2 | 4/2017 | Demos et al. | |
| 9,677,131 B2 | 6/2017 | Fredriksson et al. | |
| 2002/0106648 A1 | 8/2002 | Lizardi et al. | |
| 2003/0008313 A1 | 1/2003 | Wiltshire | |
| 2003/0124595 A1 | 7/2003 | Lizardi | |
| 2003/0124629 A1 | 7/2003 | Tse et al. | |
| 2003/0175828 A1 | 9/2003 | Lazar | |
| 2004/0241759 A1 | 12/2004 | Tozer et al. | |
| 2005/0026161 A1 | 2/2005 | Jablonski et al. | |
| 2005/0214809 A1 | 9/2005 | Han | |
| 2006/0166227 A1 | 7/2006 | Kingsmore et al. | |
| 2007/0009914 A1* | 1/2007 | Wallace ............... | C12Q 1/6804 435/6.11 |
| 2007/0166709 A1 | 7/2007 | McCreavy et al. | |
| 2008/0152207 A1 | 6/2008 | Micheva et al. | |
| 2008/0269068 A1 | 10/2008 | Church et al. | |
| 2009/0004749 A1 | 1/2009 | Yamagata et al. | |
| 2009/0111094 A1* | 4/2009 | Storhoff .......... | G01N 33/54386 435/6.11 |
| 2010/0151472 A1* | 6/2010 | Nolan .................... | C12Q 1/682 435/6.1 |
| 2010/0304994 A1 | 12/2010 | Wu et al. | |
| 2011/0223585 A1 | 9/2011 | Gullberg et al. | |
| 2013/0040840 A1 | 2/2013 | Huang et al. | |
| 2013/0123121 A1 | 5/2013 | Schwartz et al. | |
| 2013/0288249 A1 | 10/2013 | Gullberg et al. | |
| 2013/0323729 A1 | 12/2013 | Landegren et al. | |
| 2013/0344500 A1 | 12/2013 | Trautman et al. | |
| 2014/0194311 A1 | 7/2014 | Gullberg et al. | |
| 2014/0309134 A1 | 10/2014 | Xu et al. | |
| 2016/0002704 A1 | 1/2016 | Diehl et al. | |
| 2016/0161472 A1 | 6/2016 | Jungmann et al. | |
| 2016/0258956 A1 | 9/2016 | Schwartz | |
| 2016/0319328 A1* | 11/2016 | Yin ....................... | C12Q 1/6804 |
| 2017/0009278 A1 | 1/2017 | Söderberg et al. | |
| 2017/0089892 A1 | 3/2017 | Aghvanyan et al. | |
| 2017/0101665 A1 | 4/2017 | Banerjee et al. | |
| 2017/0107566 A1 | 4/2017 | Church et al. | |
| 2017/0159136 A1 | 6/2017 | Church et al. | |
| 2017/0168047 A1 | 6/2017 | Aghvanyan et al. | |
| 2017/0192013 A1 | 7/2017 | Agresti | |
| 2017/0307627 A1 | 10/2017 | Wang et al. | |
| 2018/0024139 A1 | 1/2018 | Peikon et al. | |
| 2018/0120306 A1 | 5/2018 | Kosmeder et al. | |

FOREIGN PATENT DOCUMENTS

| | | |
|---|---|---|
| EP | 1563100 B1 | 4/2013 |
| EP | 2369015 B1 | 4/2014 |
| EP | 2818867 A1 | 12/2014 |
| EP | 2593563 B1 | 11/2016 |
| EP | 2633081 B1 | 1/2017 |
| EP | 2627781 B1 | 2/2017 |
| EP | 2714925 B1 | 6/2017 |
| EP | 1771786 B1 | 12/2017 |
| WO | 2000068434 A2 | 11/2000 |
| WO | 0131056 A2 | 5/2001 |
| WO | 2001084146 A2 | 11/2001 |
| WO | 2006104979 A2 | 10/2006 |
| WO | 2012071428 A2 | 5/2012 |
| WO | 2014079802 A2 | 5/2014 |
| WO | 2014207245 A1 | 12/2014 |
| WO | 2015128490 A1 | 9/2015 |
| WO | 2015138653 A1 | 9/2015 |
| WO | 2016127149 A3 | 11/2016 |
| WO | 2017143155 A3 | 9/2017 |
| WO | 2017200870 A1 | 11/2017 |
| WO | 2017210387 A1 | 12/2017 |

OTHER PUBLICATIONS

Agasti et al., DNA-barcoded labeling probes for highly multiplexed Exchange-PAINT imaging, Chem. Sci. 2017, 8, 3080-3091.

Dirks et al., "Triggered amplification by hybridization chain reaction," PNAS Oct. 26, 2004, 101(43):15275-15278.

England, "HaloTag Technology: A Versatile Platform for Biomedical Applications," Bioconjugate Chem. 2015, 26, pp. 975-986.

Gusev et al., "Rolling Circle Amplification: A New Approach to Increase Sensitivity for Immunohistochemistry and Flow Cytometry," Amer. J. Path., Jul. 2001, 159(1):63-69.

International Search Report and Written Opinion issued in PCT/US2018/025444, dated Jun. 15, 2018, 9 pages.

Li et al., "Inhibition of Cell Proliferation by an Anti-EGFR Aptamer," PLoS One, 6(6):1-10; e20299; Jun. 2011.

Schweitzer et al., "Immunoassays with rolling circle DNA amplification: A versatile platform for ultrasensitive antigen detection," PNAS 97(18):10113-10119 (2000).

Schweller, et al., "Multiplexed in situ Immunofluorescence via Dynamic DNA Complexes," Angew Chem Int Ed Engl. Sep. 10, 2012; 51(37):9292-9296.

U.S. Appl. No. 15/836,322, filed Dec. 8, 2017.

Wang et al., Rapid Sequential in Situ Multiplexing with DNA Exchange Imaging in Neuronal Cells and Tissues, Nano Lett. 2017, 17, 6131-6139.

Xu et al., "Directed Evolution of High-Affinity Antibody Mimics Using mRNA Display," Chemistry & Biology, vol. 9, pp. 933-942, Aug. 2002.

Yin et al., "Programming biomolecular self-assembly pathways," Nature 451:318-322, Jan. 17, 2008.

Extended European Search Report issued in EP 18777112.6, dated Oct. 7, 2020, 11 pages.

Rajkovic et al., "Immunoquantitative Real-Time PCR for Detection and Quantification of *Staphylococcus aureus* Enterotoxin B in Foods," Applied and Environmental Microbiology 72(10):6593-6599.

\* cited by examiner

DNA-ANTIGEN EXCHANGE AND AMPLIFICATION

CROSS-REFERENCE TO RELATED APPLICATIONS

This application is a division of U.S. application Ser. No. 15/941,770, filed Mar. 30, 2018, which claims the benefit of priority of U.S. Provisional Application No. 62/479,676, filed Mar. 31, 2017, each of which is incorporated by reference herein in its entirety for any purpose.

FIELD

DNA-Antigen Exchange and Amplification imaging methods capable of multiplexing and increasing detection sensitivity of targets by linking a target to an antigen, an antigen-specific binding partner, and optical labels.

BACKGROUND

Secondary antibodies are raised to bind other antibodies, typically with species-specific affinity. The use of secondary antibodies in immunofluorescence applications is widespread. Secondary antibodies can be advantageous both for cost savings and signal amplification. Labeling secondary antibodies with fluorophores is more cost-effective than directly labeling primary antibodies because one type of fluorescently-labeled secondary antibody can be applied to image many different targets, provided the targets are detected on separate samples using primary antibodies from the same host species. Additionally, since multiple fluorescently-labeled secondary antibodies can bind to a single primary antibody, signal intensities generated from the sample are higher than if fluorescently-labeled primary antibodies were used. However, the use of fluorescently-labeled secondary antibodies severely limits the ability to carry out multiplexed detection. To multiplex several targets, each target-specific primary antibody must be raised in a different host species to ensure that the secondary antibodies bind to and are associated with the correct target complex. The most common host species for primary antibodies are mouse and rabbit, and the lack of high-quality alternative host species relegates the multiplexing power that is practically achievable with secondary antibodies to two targets per sample (i.e. using a labeled anti-mouse and labeled anti-rabbit secondary antibody to detect one target stained with a mouse antibody and one target stained with a rabbit antibody).

Previous approaches have tried to overcome the limitation posed by species-specific detection with secondary antibodies. Immunoreagents comprising primary antibodies attached to an antigen or hapten have been described (WO2016127149) for detection with labeled anti-antigen or anti-hapten antibodies (i.e. a detection antibody). While this approach expands the number of targets that can be labeled simultaneously, the total number of targets that can be multiplexed is still limited by the number of spectrally distinct labels that can be used to modify the detection antibodies. Furthermore, once a sample is stained, the signal from the detection antibody is fixed and cannot be removed unless stringent conditions are applied that may damage the sample. In order to achieve higher levels of multiplexing, a sequential multiplexing approach is required that is gentle enough to maintains the integrity of the sample.

Here, we present novel approaches for highly multiplexed target detection that achieves similar levels of convenience and improved amplification to that associated with labeled secondary antibodies. This approach is called DNA-Antigen Exchange and Amplification. DNA-Antigen Exchange and Amplification enables sequential multiplexing of targets and dynamic adjustments of amplification levels on a single sample.

SUMMARY

In accordance with the description, at least one method comprises (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with antigen-bound imager strands and antigen-specific binding partners linked (directly or indirectly) to optical labels, wherein the antigen-bound imager strands have complementarity to a docking strand, directly or indirectly, and wherein each antigen-specific binding partner is linked to one or more optical labels, and wherein antigen-specific binding partners of different specificity are linked to distinct optical labels, (4) optionally removing unbound antigen-bound imager strands and/or antigen-specific binding partners, (5) imaging the sample to detect bound labeled antigen-specific binding partners, (6) optionally removing/extinguishing signal from the optical labels (i.e., signal termination), and (7) optionally repeating steps (1)-(7), or any subset thereof (such as (1)-(6) or other subset, keeping in mind some steps may not be repeated, especially the signal termination step).

In some embodiments a method comprises (1) contacting a sample being tested for the presence of one or more targets with one or more target-specific binding partners, wherein each target-specific binding partner is linked to an antigen, and wherein target-specific binding partners of different specificity are linked to different antigens, (2) optionally removing unbound target-specific binding partners, (3) contacting the sample with antigen-specific binding partners linked to docking strands, wherein different antigen-specific binding partners are linked to different docking strands, (4) optionally removing unbound antigen-specific binding partners linked to docking strands; (5) adding imager strands; wherein the imager strands have complementarity to a docking strand, directly or indirectly, and wherein each imager strand is linked (directly or indirectly) to one or more optical labels, and wherein imager strands of different specificity are linked to distinct optical labels, (6) optionally removing unbound imager strands, (7) imaging the sample to detect bound labeled antigen-specific binding partners, (8) optionally removing/extinguishing signal from the optical labels (i.e., signal termination), and (9) optionally repeating steps (1)-(9), or any subset thereof (such as (1)-(8) or other subset, keeping in mind some steps may not be repeated, especially the signal termination step).

In some embodiments, a method comprises (1) contacting a sample being tested for the presence of one or more targets with one or more target-specific binding partners, wherein each target-specific binding partner is linked to a first docking strand, and wherein target-specific binding partners of different specificity are linked to different docking strands, (2) optionally removing unbound target-specific binding partners, (3) contacting the sample with antigen-bound imager strands and antigen-specific binding partners, wherein the antigen-bound imager strands have complementarity to a docking strand, directly or indirectly, and wherein each antigen-specific binding partner is linked to at least one second docking strand; (4) optionally removing unbound antigen-bound imager strands and/or antigen-specific binding partners, (5) increasing the number of second docking strand strands by a DNA amplification reaction and labeling of the second docking strands using an optical label, (6) imaging the sample to detect bound labeled antigen-specific binding partners, (7) optionally removing/extinguishing signal from the optical labels (i.e., signal termination), and (8) optionally repeating steps (1)-(8), or any subset thereof (such as (1)-(7) or other subset, keeping in mind some steps may not be repeated, especially the signal termination step).

In some embodiments, a method comprises (1) contacting a sample being tested for the presence of one or more targets with one or more target-specific binding partners, wherein each target-specific binding partner is linked to an antigen, and wherein target-specific binding partners of different specificity are linked to different antigens, (2) optionally removing unbound target-specific binding partners, (3) contacting the sample with antigen-specific binding partners linked docking strands, wherein different antigen-specific binding partners are linked to different docking strands, (4) optionally removing unbound antigen-specific binding partners linked to docking strands; (5) increasing the number of docking strands by a DNA amplification reaction and labeling of the docking strands using an optical label, (6) imaging the sample to detect bound labeled antigen-specific binding partners, (7) optionally removing/extinguishing signal from the optical labels (i.e., signal termination), and (8) optionally repeating steps (1)-(8), or any subset thereof (such as (1)-(7) or other subset, keeping in mind some steps may not be repeated, especially the signal termination step).

In some embodiments, a composition comprises (1) a first binding partner-oligonucleotide conjugate comprising a binding partner linked to an oligonucleotide that comprises a docking domain; (2) an antigen-bound oligonucleotide conjugate comprising an antigen linked to an oligonucleotide that comprises an imager domain, wherein the imager domain of (2) is complementary to the docking domain of (1); and (3) a labeled antigen-specific binding partner comprising an optical label linked to an antigen-specific binding partner, wherein the antigen-specific binding partner of (3) specifically binds the antigen in (2).

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1A shows a target-specific binding partner (102) attached to a docking strand (103) binds to a target (101) in a sample. An imager strand (104) comprising an antigen (105) is added to bind to the docking strand. An antigen-specific binding partner (106) attached to optical labels (107) is added to the sample to bind the antigen that is complexed on the target. At this stage, the sample can be imaged to detect the signal and identify the target. Finally, an exchange reaction (108) can be carried out to remove the signal. FIG. 1B shows DNA-Antigen amplification scheme via a layering approach wherein a target-specific binding partner (102) attached to a docking strand (103) binds to a target (101) in a sample. An imager strand (104) comprising an antigen (105) is added to bind to the docking strand. An antigen-specific binding partner (106) is added to the sample to bind the antigen that is complexed on the target. An anti-antigen-specific binding partner (109) attached to optical labels (107) is added to the sample to bind to the target through the layered complex. At this stage, the sample can be imaged to detect the signal and identify the target. Finally, an exchange reaction (not shown) can be optionally carried out to remove the signal. FIG. 1C shows a target-specific binding partner (102) attached to an antigen (105) binding to a target (101) in a sample. An antigen-specific binding partner (106) attached to docking strands (103) is added to the sample to bind the antigen that is complexed on the target. An imager strand (104) comprising an optical label (107) is added to bind to the docking strands. At this stage, the sample can be imaged to detect the signal and identify the target. Finally, an exchange reaction (not shown) can be optionally carried out to remove the signal. FIG. 1D shows a target-specific binding partner (102) attached to an antigen (105) binding to a target (101) in a sample. An antigen-specific binding partner (106) attached to docking strands (103) is added to the sample to bind the antigen that is complexed on the target. Optionally, the number of docking strands complexed to the targets are increased by a DNA amplification reaction (110) such as rolling circle amplification. An imager strand (104) comprising an optical label (107) is added to bind to the docking strands. At this stage, the sample can be imaged to detect the signal and identify the target. Finally, an exchange reaction (108) can be optionally carried out to remove the signal. FIG. 1E shows a target-specific binding partner (102) attached to a docking strand (103) binds to a target (101) in a sample. An imager strand (104) comprising an antigen (105) is added to bind to the docking strand. An antigen-specific binding partner (106) attached to docking strands (103) is added to the sample to bind the antigen that is complexed on the target. Optionally, the number of docking strands complexed to the targets are increased by a DNA amplification reaction (110) such as rolling circle amplification. An imager strand (104) comprising an optical label (107) is added to bind to the docking strands. At this stage, the sample can be imaged to detect the signal and identify the target. Finally, an exchange reaction (108) can optionally be carried out to remove the signal. FIG. 1F shows a target-specific binding partner (102) attached to a docking strand (103) binds to a target (101) in a sample. An imager strand (104) comprising an antigen (105) is added to bind to the docking strand. An antigen-specific binding partner (106) is added to the sample to bind the antigen that is complexed on the target. An anti-antigen-specific binding partner (109) attached to docking strands (103) is added to the sample to bind to the target through the layered complex. Optionally, the number of docking strands complexed to the targets are increased by a DNA amplification reaction (110) (product not shown). An imager strand (104) comprising an optical label (107) can be added to bind to the docking strands complexed to the target. At this stage, the sample can be imaged to detect the signal and identify the target. Finally, an exchange reaction (108) can optionally be carried out to remove the signal. While FIG. 1F is shown as a variant of FIG. 1E, it may also be carried out with primary antibodies directly conjugated to antigens, such as FIG. 1D instead of primary antibodies conjugated to docking strands, such as in FIG. 1E.

FIG. 2A shows a blank image of prepared sample. FIG. 2B shows an Image of Ki67 in sample following addition of imager strand I1-bio and SA-Cy5. FIG. 2C shows a sample image after exchange step removing I1-bio and SA-Cy5. FIG. 2D shows an image of cytokeratin in sample following addition of imager strand I2-bio and SA-Cy5.

Figure 1A:
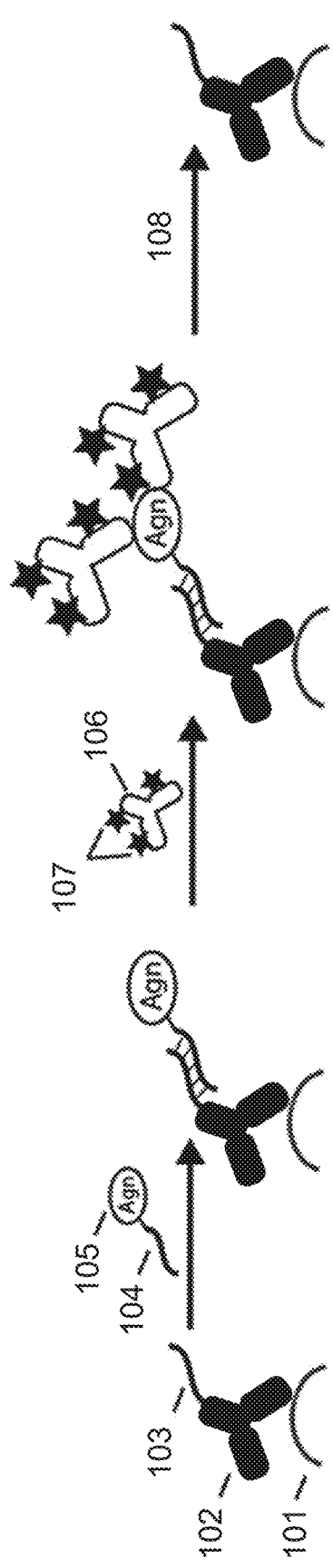
FIGS. 1A-F provide schemes of DNA-Antigen Amplification and Exchange.

The following reference numbers are employed in the application:'

TABLE 1

| | Reference Numbers |
|---|---|
| 101 | Target |
| 102 | Target-specific binding partner |
| 103 | docking strand |
| 104 | imager strand |
| 105 | antigen |
| 106 | antigen-specific binding partner |
| 107 | optical label |
| 108 | Exchange reaction |
| 109 | Secondary binding partner (such as but not limited to, an anti-antigen-specific binding partner) |
| 110 | DNA amplification reaction |

DESCRIPTION OF THE EMBODIMENTS

I. Multiplexed Imaging Using DNA-Antigen Exchange Amplification

This application relates to methods and compositions for testing for the presence of one or more target(s) with one or more specific binding partner(s). Components may be complexed together through a series of binding interactions to link a target to a detection element.

Exchange imaging is a method to achieve high multiplexing capabilities, whereby a large number of targets can be imaged in the same sample, either simultaneously or sequentially. Exchange imaging relies on the ability to introduce detectable moieties that bind (e.g. through a molecular complex) specifically to one or more target(s) in a sample, wherein different target types are bound to distinct detectable moieties, and then subsequently the ability to remove the detectable moieties from the sample. A target in a sample that is bound to a target-specific binding agent attached to a docking strand that is attached to an antigen-bound imager strand can then be detected by introducing an antigen-specific binding partner that is attached to one or more detectable labels. The resulting signal can then be optionally removed. In one example, the signal is removed by disrupting the binding affinities between the docking and imager strands.

Signal amplification is often beneficial for low abundance targets, or when the sensitivity of the imaging equipment is low. Signal amplification covers the concept of increasing the number of detectable elements that are specifically bound to a target. In one non-limiting example, signal amplification results from increasing the number of fluorophores associated with a target. Signal amplification approaches can be combined with DNA-antigen Exchange methods to yield greater assay sensitivity, dynamic range, and greater content generation. Here, we discuss embodiments covering DNA-antigen exchange and signal amplification.

In some embodiments, a method of DNA-Antigen Exchange comprises (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with antigen-bound imager strands and antigen-specific binding partners linked (directly or indirectly) to optical labels, (a) wherein the antigen-bound imager strands have complementarity to a docking strand, directly or indirectly, and (b) wherein each antigen-specific binding partner is linked to one or more optical labels, and wherein antigen-specific binding partners of different specificity are linked to distinct optical labels, (4) optionally removing unbound antigen-bound imager strands and/or antigen-specific binding partners, (5) imaging the sample to detect bound labeled antigen-specific binding partners, (6) optionally removing/extinguishing signal from the optical labels (i.e., signal termination), and (7) optionally repeating steps (1)-(7), or any subset thereof (such as (1)-(6) or other subset, keeping in mind some steps may not be repeated, especially the signal termination step).

By optionally removing/extinguishing the signal from the optical labels, we mean any step that causes the signal to terminate. This can include removing the antigen-bound imager strands from the docking strands, cleaving or degrading the imager strand and/or the docking strands, photobleaching the label or otherwise extinguishing its signal, or removing the label from the moiety to which it has been attached. Such a signal termination step may completely eliminate the signal from the optical label or it may substantially reduce the signal from the optical label with a reduction of signal of at least 99%, 95%, 90%, 85%, 80%, 75%, 70%, 60%, or 50%.

In some methods, the antigen-specific binding partners and antigen-bound imager strands are added stepwise in the method herein. Namely, the method of DNA-Antigen Exchange comprises (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with antigen-bound imager strands having complementarity to a docking strand, directly or indirectly, (4) optionally removing unbound antigen-bound imager strands, (5) contacting the sample with labeled antigen-specific binding partner, wherein each antigen-specific binding partner is linked to one or more optical labels, and wherein antigen-specific binding partners of different specificity are linked to distinct optical labels, (6) optionally removing unbound antigen-specific binding partners, (7) imaging the sample to detect bound labeled antigen-specific binding partners, (8) optionally removing/extinguishing signal from the optical labels (i.e., signal termination), and (9) optionally repeating steps (1)-(9), or any subset thereof (such as (1)-(8) or other subset, keeping in mind some steps may not be repeated, especially the signal termination step).

In some other embodiments, the antigen-specific binding partners and antigen-bound imager strands are premixed before including them in the method herein. Namely, the method of DNA-Antigen Exchange comprises (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with labeled antigen-specific binding partners, wherein each antigen-specific binding partner is linked to one or more optical labels, wherein antigen-specific binding partners of different specificity are linked to distinct optical labels, and wherein the labeled antigen-specific binding partners are bound to antigen-bound imager strands having complementarity to a docking strand, directly or indirectly, (4) optionally removing unbound labeled antigen-specific binding partners and antigen-bound imager strands, (5) imaging the sample to detect bound labeled antigen-specific binding partners, (6) optionally removing/extinguishing signal from the optical labels (i.e., signal termination), and (7) optionally repeating steps (1)-(7), or any subset thereof (such as (1)-(6) or other subset, keeping in mind some steps may not be repeated, especially the signal termination step).

In some embodiments, steps (3) and (4) together comprise: (a) first contacting the sample with antigen-bound imager strands, (b) second optionally removing unbound antigen-bound imager strands, (c) third contacting the sample with labeled antigen-specific binding partner, and (d) fourth optionally removing unbound antigen-specific binding partners.

In some embodiments, step (3) comprises contacting the sample with antigen-specific binding partners, wherein the antigen-specific binding partners are bound to antigen-bound imager strands. By bound, Applicant intends to include both covalent and noncovalent binding.

In some embodiments, steps (3) and (4) together comprise (a) increasing the observable signal by contacting the sample with antigen-bound imager strands having complementarity to a docking strand, directly or indirectly, (b) optionally removing unbound antigen-bound imager strands, (c) contacting the sample with labeled antigen-specific binding partner, wherein each antigen-specific binding partner is linked to one or more optical labels, and wherein antigen-specific binding partners of different specificity are linked to distinct optical labels, and (d) optionally removing unbound antigen-specific binding partners.

In some embodiments, the method includes removing antigen-bound imager strands not bound to docking strands. In some embodiments, the method includes removing antigen-specific binding partners not bound to antigen-bound imager strands.

II. DNA-Antigen Amplification

The ability to dynamically adjust the level of signal amplification allows for greater flexibility in experimental workflow, sample preparation, and assay development. The level of target expression may vary from sample to sample. Thus, it is beneficial to be able to adjust the signal amplification level while an experiment is in progress. One may first prepare a sample and image without any amplification. Upon imaging, if the signal is found to be low, one may wish to exchange the unamplified detection reagents for amplified detection reagents. Alternatively, amplification may be used on a sample before any imaging has been conducted.

In one embodiment, DNA-antigen amplification can be used to functionally characterize assay reagents. For example, DNA-antigen amplification can be applied to validate or quality check the production of antibody-DNA conjugates.

In one embodiment, DNA-antigen amplification is employed to detect a plurality of targets in a sample. In another embodiment, target-specific binding partners from the same host-species are used to bind to a plurality of targets in a sample. In one non-limiting example, a plurality of primary antibodies derived from the same host species are bound to a plurality of targets and detected with DNA-antigen amplification.

A. DNA-Antigen Amplification for Dynamic Signal Adjustment

The embodiments described herein can be used after an initial imaging step where the user determines whether the signal is strong enough or requires amplification. In an initial imaging step, the sample may be contacted with one or more target-specific binding partner linked to a docking strand, wherein target-specific binding partners of different specificity are linked to different docking strands. As a "preview" or initial imaging step, the sample is then contacted with labeled imager strands having complementarity to a docking strand, directly or indirectly, the sample imaged, and the bound labeled imager strands removed. This initial "preview" imaging step would not employ antigen-bound imager strands and antigen-specific binding partners unless the user determined that the initial imaging step with the labeled imager strands did not produce a sufficient signal. If amplification is desired, the user can shift into an amplification mode using antigen-bound imager strands and labeled antigen-specific binding partners. The application terms this function "dynamic signal adjustment" because the antigen-bound imager strands and antigen-specific binding partners may be employed for amplification during the workflow of an exchange imaging method.

Thus, in some embodiments, a method of DNA-Antigen Amplification comprises (1) contacting a sample being tested for the presence of one or more targets with one or more target-specific binding partners, wherein each target-specific binding partner is linked to a docking strand, and wherein target-specific binding partners of different specificity are linked to different docking strands, (2) optionally removing unbound target-specific binding partners, (3) contacting the sample with labeled imager strands having complementarity to a docking strand, directly or indirectly, (4) optionally removing unbound labeled imager strands, (5) imaging the sample to detect bound labeled imager strands, (6) removing bound labeled imager strands, (7) increasing the observable signal by contacting the sample with antigen-bound imager strands having complementarity to a docking strand, directly or indirectly, (8) optionally removing unbound antigen-bound imager strands, (9) contacting the sample with labeled antigen-specific binding partner, wherein each antigen-specific binding partner is linked to one or more optical labels, and wherein antigen-specific binding partners of different specificity are linked to distinct optical labels, (10) optionally removing unbound antigen-specific binding partners, (11) imaging the sample to detect bound labeled antigen-specific binding partners, (12) optionally removing/extinguishing signal from the optical labels (i.e., signal termination), and (13) optionally repeating steps (1)-(13), or any subset thereof (such as (1)-(12) or other subset, keeping in mind some steps may not be repeated, especially the signal termination step).

In some embodiments, between steps (2) and (3), the method comprises: (a) contacting the sample with labeled imager strands having complementarity to a docking strand, directly or indirectly, (b) optionally removing unbound labeled imager strands, (c) imaging the sample to detect bound labeled imager strands, and (d) removing bound labeled imager strands.

B. DNA-Antigen Amplification Composition

In one embodiment, a composition is described comprising (a) a first binding partner-oligonucleotide conjugate comprising a binding partner linked to an oligonucleotide that comprises a docking domain; (b) an antigen-bound oligonucleotide conjugate comprising an antigen linked to an oligonucleotide that comprises an imager domain, wherein the imager domain of (b) is complementary to the docking domain of (a); and (c) a labeled antigen-specific binding partner comprising an optical label linked to an antigen-specific binding partner, wherein the antigen-specific binding partner of (c) has specificity for the antigen in (b).

C. Employing Secondary Binding Partners for Amplification

In some embodiments, secondary binding partners linked to optical labels are introduced, wherein the secondary binding partners specifically bind the antigen-specific binding partners, directly or indirectly. This allows for layering of additional binding partners linked to optical labels for a stronger signal. When the secondary binding partner binds directly, the secondary binding partner may be, thus, an anti-antigen-specific binding partner.

In some embodiments, the secondary binding partners and the antigen of the antigen-bound imager strands each comprise the same antigen. This means that at least part of the secondary binding partner and the antigen are identical, even though the secondary binding partner is bound to an optical label and the antigen is bound to an imager strand. In other embodiments, the secondary binding partners and the antigen of the antigen-bound imager strands may comprise different antigens, in other words, the secondary binding partners may not, in this embodiment, comprise the antigen of the antigen-bound imager strands.

In some embodiments, the antigen and the secondary binding partner each comprise biotin. In some embodiments, the antigen-specific binding partner comprises streptavidin.

In some embodiments, the secondary binding partner binds the antigen-specific binding partner indirectly. For example, if the antigen is biotin and the antigen-specific binding partner is streptavidin, the secondary binding partner may also be streptavidin if a construct employing two biotin moieties conjugated by a linker was used. This embodiment may have advantages when an even stronger signal is desired because it may be possible to conjugate more copies of a label to streptavidin than biotin. The construct employing two biotin moieties can thus serve as a bridge enabling specific binding of the secondary binding partner to the antigen-specific binding partner.

In some embodiments, the antigen-specific binding partners and the secondary binding partners both comprise an antibody or an antigen-binding fragment thereof.

In some instances, the antigen-specific binding partner is a primary antibody or antigen-binding fragment thereof to the antigen and the secondary binding partner is a secondary antibody or antigen-binding fragment thereof.

In some embodiments, multiple antigen-specific binding partners bind to a single antigen. In some embodiments, the antigen-specific binding partners comprise a polyclonal antibody. In some embodiments, multiple types of antigen-specific binding partners are used. For instance, the multiple types of antigen-specific binding partners may comprise more than one monoclonal antibody directed to different epitopes on the antigen.

In some embodiments, multiple layers of amplification may be employed so that multiple secondary antibodies are layered on top of each other. For instance, the first secondary antibody could bind to the antigen and a second secondary antibody (i.e., a tertiary antibody) could bind to the first secondary antibody and so on. A third secondary antibody (i.e., a quaternary antibody) could bind to the second secondary antibody, and so on. The number of layers employed depends on the amplification desired and other factors, as follows.

When employing secondary binding partners for amplification, some layered complexes may be removable by washing steps. Other layered complexes may not be removable by washing steps. Those that are removable may be used for exchange imaging with amplification. Those that are not removable may be used for amplification and for the last imaging step in an exchange imaging reaction.

III. Components

A. Targets

In certain embodiments, the target-specific binding partner is specific for a cellular marker. Cellular markers may include: 4-1BB, AFP, ALK1, Amyloid A, Amyloid P, Androgen Receptor, Annexin A1, ASMA, BCA225, BCL-1, BCL-2, BCL-6, BerEP4, Beta-Catenin, Beta-HCG, BG-8, BOB-1, CA19-9, CA125, Calcitonin, Caldesmon, Calponin-1, Calretinin, CAM 5.2, CD1a, CD2, CD3, CD4, CD5, CD7, CD8, CD10, CD15, CD19, CD20, CD21, CD22, CD23, CD25, CD30, CD31, CD33, CD34, CD38, CD42b, CD43, CD45 LCA, CD45RO, CD56, CD57, CD61, CD68, CD79a, CD99, CD117, CD138, CD163, CDX2, CEA, Chromogranin A, CMV, c-kit, c-MET, c-MYC, Collagen Type IV, Complement 3c (C3c), COX-2, CXCR5, CK1, CK5, CK6, CK7, CK8, CK14, CK18, CK17, CK19, CK20, CK903, CK AE1, CK AE1/AE3, D2-40, Desmin, DOG-1, E-Cadherin, EGFR, EMA, ER, ERCC1, Factor VIII-RA, Factor XIIIa, Fascin, FoxP1, FoxP3, Galectin-3, GATA-3, GCDFP-15, GCET1, GFAP, Glycophorin A, Glypican 3, Granzyme B, HBME-1, *Helicobacter Pylori*, Hemoglobin A, Hep Par 1, HER2, HHV-8, HMB-45, HSV 1/11, ICOS, IFNgamma, IgA, IgD, IgG, IgM, IL17, IL4, Inhibin, iNOS, Kappa Ig Light Chain, Ki67, LAG-3, Lambda Ig Light Chain, Lysozyme, Mammaglobin A, MART-1/Melan A, Mast Cell Tryptase, MLH1, MOC-31, MPO, MSA, MSH2, MSH6, MUC1, MUC2, MUM1, MyoD1, Myogenin, Myoglobin, Napsin A, Nestin, NSE, Oct-2, OX40, OX40L, p16, p21, p27, p40, p53, p63, p504s, PAX-5, PAX-8, PD-1, PD-L1, PHH3, PIN-4, PLAP, PMS2, *Pneumocystis jiroveci (carinii)*, PR, PSA, PSAP, RCC, S-100, SMA, SMM, Smoothelin, SOX10, SOX11, Surfactant Apoprotein A, Synaptophysin, TAG 72, TdT, Thrombomodulin, Thyroglobulin, TIA-1, TIM3, TRAcP, TTF-1, Tyrosinase, Uroplakin, VEGFR-2, Villin, Vimentin, and WT-1. In other embodiments, the target-specific binding partner is specific for an immunoglobulin from a different species.

B. Target-Specific Binding Partners

The target specific binding partner refers to antibodies and antibody-like molecules that can be used to detect the target molecule. Antibody refers to any immunoglobulin from any species that can specifically recognize a target molecule. Antibody-like molecule refers to (Class A) any engineered variation or fragment of an antibody such as Fab, Fab', F(ab')2, single heavy chain, diabody, and the like (antigen binding fragments of antibodies) (Class B) any known binding partner of a target molecule and engineered variants of such binding partner, (Class C) any binding partner of the target molecule engineered via directed evolution (e.g., peptides and aptamers), and (Class D) any molecule that selectively forms covalent bond(s) with a target (e.g., a suicide substrate of an enzyme of interest). References to specific types of antibodies throughout the specification encompass both full length antibodies and any antibody-like molecules that include any engineered variation or fragments of an antibody such as Fab, Fab', F(ab')2, single heavy chain, diabody, and the like (antigen binding fragments of antibodies). Thus, for example, in Table 2, when the target recognition moiety references antibody, it also includes antigen binding fragments of those antibodies.

The target-specific binding partner may be provided in a liquid medium or buffer solution. Target-specific binding partners for different targets may be contacted with a sample in a single step or in multiple steps, such as after a prior imaging step.

Table 2 provides a representative listing of targets and corresponding target recognition moieties.

TABLE 2

Representative Targets and Target Recognition Moieties

| Target | Target Recognition Moiety | Source or Sequence |
|---|---|---|
| Any protein | Antibody (Class A) | Variable |
| Fluorescein (chemical compound) | Antibody (Class A) | Abcam, product # ab7253 |
| Digoxigenin (chemical compound) | Antibody (Class A) | Abcam, product # ab76907 |
| Biotin | Avidin/Streptavidin (Class B) | |
| Epidermal growth factor receptor (EGFR, protein) | Epidermal growth factor (EGF, Class B) | |
| Platelet-derived growth factor receptor (PDGFR, protein) | Platelet-derived growth factor (PDGF, Class B) | |
| Epidermal growth factor receptor (EGFR, protein) | E07 aptamer (Class C) | Li et al., PloS ONE, 2011; 6(6): e20299 |
| Integrins (protein) | RGD-containing peptides (Class B) | |
| TNF-α (protein) | T09.12 peptide (Class C) | Xu et al., Chem Biol. 2002 Aug; 9(8): 933-42. |
| HaloTag (enzyme) | Halogenated compounds (Class D) | Bioconjug Chem. 2015 Jun 17; 26(6): 975-86. |
| Oxidosqualene cyclase (OSC, enzyme) | [3H]29-methylidene-2,3-oxidosqualene ([3H]29-MOS, Class D) | Biochem Biophys Res Commun. 1992 Aug 31; 187(1): 32-8. |

Table 3 provides a listing of additional targets. Antibodies and other known binding partners of these targets may be used as target recognizing moieties.

TABLE 3

Additional Representative Targets

Actin
AIF
AKT
alpha-synuclein
amyloid precursor protein
annexin
Arrestin
BAD
BAX
Bcl-2
Bcl-2
beta-catenin
BRCA1
cAMP
Caveolin
CD20
CD3
CD4
CD45
CD68
CD8
collagen
CREB
DNA
E-Cadherin
EGFR
EpCAM
ER
ERK
ERK
FOXA
FOXP3
GABA
GAPDH
GFP
GranzymeB
GRB2
HER2
HER3
HIF-1
HistoneH3
HSP27
HSP70
HSP90
keratin
Ki67
Lamin
MAPK
MEK
MET
MMP
mTOR
MYC
NeuN
p21
p53
PAX
PD-1
PD-L1
PI3K
PR
PSD95
RAS
SOX
STAT
synapsin
Tau
TOM20
Tubulin
Ubiquitin
VEGF
Vimentin
WNT

C. Docking Strands

In some embodiments, the docking moiety or docking strand is a nucleic acid, a protein, a peptide, or a chemical compound. Many proteins and domains of proteins are known to interact with other proteins, domains or peptides. Some of the best-known domains include SH2, SH3, and WD40 domains. In many cases the binding partner of these proteins and domains are known and can be engineered to have the desired affinity. For example, biotin and avidin/streptavidin interact with sufficient specificity. Many other chemical compounds, such as digoxigenin, fluorescein, tacrolimus and rapamycin also have well known binding partners.

In some embodiments, the docking strand comprises nucleic acids. In some embodiments, the nucleic acids are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the docking strand is attached to the imager strand covalently and in other embodiments noncovalently.

In some embodiments, the docking strand comprises single-stranded nucleic acids and may be from about 5 to 20 nucleic acids long, from about 8 to 15, or from about 10 to 12 nucleic acids long. In some embodiments, the docking strand is about 5, 8, 9, 10, 11, 12, 13, 14, 15, 18, or 20 nucleic acids long.

The docking strand may be an independent element or it may be part of the target recognizing moiety. For example, if the target recognizing moiety is an antibody, part of the Fc domain of the antibody may be the docking strand and a peptide or protein that binds the Fc domain may be used, such as protein A or protein G.

The docking strand may be provided in a liquid medium or buffer solution.

D. Imager Strands

The imager strand may be any molecule that is complementary to the docking strand (i.e., capable of specific binding to the docking strand) and attached (either directly or indirectly) to an antigen. In some embodiments, the docking strand may be a nucleic acid strand, a protein, a peptide, or a chemical compound. In such cases, the observable moiety or label may be conjugated to an imager moiety, which may be a nucleic acid strand that is complementary to the docking strand. In other words, the imager strand specifically binds the docking strand. In such a case, the label may be conjugated to an imager moiety that may be from about 5 to 20 nucleic acids long, from about 8 to 15, or from about 10 to 12 nucleic acids long. In some embodiments, the imager moiety is about 5, 8, 9, 10, 11, 12, 13, 14, 15, 18, or 20 nucleic acids long.

In some embodiments, the complementary portions between the imager moiety and the docking strand may be from about 5 to 20 nucleic acids long, from about 8 to 15, or from about 10 to 12 nucleic acids long nucleic acids long. In some embodiments, the complementary portions between the imager moiety and the docking strand may be about 5, 8, 9, 10, 11, 12, 13, 14, 15, 18, or 20 nucleic acids long.

In some embodiments, the nucleic acid imager strand comprises single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the imager moiety is a protein, peptide, or a chemical compound, as a partner to the docking strand options discussed above in Section III.C above.

In some embodiments, the docking strand may bind to the imager moiety indirectly, such as through an intermediate moiety. For instance, when the docking strand and the imager moiety are nucleic acids, an intermediate moiety comprising nucleic acids may be used as long as the intermediate moiety has a first region complementary to the docking strand and a second region complementary to the imager moiety. In this embodiment, it is not necessary for the docking strand to be complementary to the imager moiety. The intermediate moiety may serve only a bridging function or it may also serve an amplification function.

The imager strand may be provided in a liquid medium or buffer solution.

E. Intermediate Strands

In some instances, the docking strand binds to the imager strand through an intermediate moiety (or intermediate strand). For instance, when the docking moiety and the imager moiety comprise nucleic acids, the intermediate strand comprising nucleic acids may be used as long as the intermediate strand has a first region complementary to the docking strand and a second region complementary to the imager strand. In such embodiments, it is not necessary for the docking strand to be complementary to the imager moiety.

In some embodiments, the intermediate strand is added as a first step to a sample comprising the target-specific binding partner linked to a docking strand, either directly or indirectly, and the imager strands added as a second step. In another embodiment, the intermediate strand and imager strand are not added in discrete steps. In some instances, the intermediate strand and imager strand are hybridized together before being added in a single step.

In some embodiments, the intermediate strand comprises nucleic acids. In some embodiments, the nucleic acids are single stranded nucleic acids such as single stranded DNA, RNA, or a nucleic acid analog. A nucleic acid analog (also known as non-natural nucleic acid) may include an altered phosphate backbone, an altered pentose sugar, and/or altered nucleobases. Nucleic acid analogs may include, but are not limited to, 2'-O-Methyl ribonucleic acid, 2'-fluoro ribonucleic acid, peptide nucleic acid, morpholino and locked nucleic acid, glycol nucleic acid, and threose nucleic acid.

In some embodiments, the intermediate strand comprises single-stranded nucleic acids and may be from about 5 to 30 nucleic acids long, from about 8 to 15, or from about 10 to 12 nucleic acids long. In some embodiments, the intermediate strand is about 5, 8, 9, 10, 11, 12, 13, 14, 15, 18, 20, 25, or 30 nucleic acids long.

The intermediate strand may be provided in a liquid medium or buffer solution.

F. Antigens

Antigens could include haptens, small molecules, proteins, or immunogenic molecules. For example, antigens could include but not be limited to digoxigenin, biotin, avidin, streptavidin, horseradish peroxidase (HRP), albumin, bovine serum albumin, keyhole limpet hemocyanin, *Concholepas concholepas* hemocyanin, Ovalbumin, alkaline phosphatase, protein-C, or derivatives thereof. Antigens could include molecules such as nitrophenyl, dinitrophenyl, trinitrophenyl, digitoxin, 5-bromodeoxyuridine, 3-nitrotyrosine, benzylguanine, benzylcytosine, melamine, small-molecule drugs, and any other similar chemical tag. Antigens could include a Myc tag, a FLAG tag, a SNAP tag, a CLIP tag, an HA tag, an S tag, a Streptag, a His tag, or a V5 tag. Antigens could be antibodies (e.g. IgG, IgM, IgA, IgD, IgE, etc), antibody fragments (Fab, Fab', F(ab')$_2$, Fc, pFc', single-chain variable fragment (scFv), di-scFv, single-domain antibody (sdAb), nanobody). Antigens could include any cellular marker listed as a target in this application, for example those proteins listed in Table 3.

Antigens could be nucleic acids or aptamers, including but not limited to, non-natural nucleic acids and oligomers. Antigens could be polymers (e.g. amino acid oligomers, peptides, cellulose, pectin, polyethylene, polyethylene glycol (PEG), dextran, cyclodextrin, nylon, Teflon, polystyrene, PVC, polypropylene) or molecular imprints (MIPs). Antigens could be organic fluorophores (e.g. Alexa Fluor dyes, Atto dyes, fluorescein (FITC)), fluorescent or chemiluminescent proteins (e.g. GFP, RFP, YFP, mCherry, phycoerythrin). Antigens could be mis-folded or denatured proteins. Antigens could be nanoparticles or coated nanoparticles. Antigens may be produced through chemical synthesis, be naturally occurring, be recombinantly expressed or genetically engineered.

Antigens may be linear, circular, branched, polymeric, or dendritic. Antigens may have one or more epitopes and may bind to one or more antigen-specific binding partners. One or more distinct species of antigen-binding partners may bind to the same antigen at different epitopes.

G. Antigen-Specific Binding Partners

The antigen-specific binding partner may refer to antibodies and antibody-like molecules that can be used to detect an antigen. Antibody refers to any immunoglobulin from any species that can specifically recognize a target molecule or antigen. Antibody-like molecule refers to (Class A) any engineered variation or fragment of an antibody such as Fab, Fab', F(ab')2, single heavy chain, diabody, and the like (antigen binding fragments of antibodies) (Class B) any known binding partner of an antigen molecule and engineered variants of such binding partner, (Class C) any binding partner of the antigen molecule engineered via directed evolution (e.g., peptides and aptamers), and (Class D) any molecule that selectively forms covalent bond(s) with an antigen (e.g., a suicide substrate of an enzyme of interest).

An antigen-specific binding partner may also be a protein with high affinity for an antigen. For example, streptavidin may be used as a binding partner in the case where biotin is used as the antigen. If the antigen is a metal ion, an antigen-specific binding partner may be a chelating agent, such as EDTA, ethylenediamine, polyhistidine, heme, porphine, crown ether, cryptand, or another polydentate ligand.

An antigen-specific binding partner may form a covalent or noncovalent association with an antigen.

Antigen-specific binding partners corresponding to different targets may be contacted with a sample in a single step or in multiple steps, such as after a prior imaging step.

Antigens of antigen-bound imager strands and antigen-specific binding partners are described in pairs in Table 4.

TABLE 4

Pairings of Antigens of Antigen-Bound Imager Strands and Antigen-Specific Binding Partners

| Antigens of Antigen-Bound Imager Strands | Antigen-Specific Binding Partners |
|---|---|
| Any protein or peptide | Immunoglobin (namely an antibody or antigen binding fragment thereof that specifically binds the protein or peptide) |
| Any protein or peptide | Aptamer |
| Biotin | Streptavidin |
| Streptavidin | Biotin |
| Horseradish Peroxidase (HRP) | Anti-HRP antibody or antigen binding fragment thereof |
| Anti-HRP antibody or antigen binding fragment thereof | Horseradish Peroxidase (HRP) |
| Alkaline Phosphatase (AP) | Anti-AP antibody or antigen binding fragment thereof |
| Any epitope tag | Anti-epitope antibody or antigen binding fragment thereof |
| Myc tag | Anti-myc antibody or antigen binding fragment thereof |
| FLAG tag | Anti-FLAG antibody or antigen binding fragment thereof |
| SNAP tag | benzylguanine |
| CLIP tag | benzylcytosine |
| benzylguanine | SNAP tag |
| benzylcytosine | CLIP tag |
| Histidine tag | Metal ions |
| Metal ion | Chelating agent (such as EDTA, ethylenediamine, polyhistidine, heme, porphine, crown ether, cryptand, or other polydentate ligand) |
| IgG (namely a primary antibody) | Anti-IgG antibody or antigen binding fragment thereof (namely a secondary antibody that specifically binds to the primary antibody and using the terminology herein this antibody binds to the antigen antibody of the antigen-bound imager strand) |
| Fc fragment | Anti-Fc antibody or antigen binding fragment thereof |
| Any fluorophore | Antibody or antigen binding fragment thereof |
| GFP | Anti-GFP antibody or antigen binding fragment thereof |
| Anti-GFP antibody or antigen binding fragment thereof | GFP |
| Fluorescein | Anti-fluorescein antibody or antigen binding fragment thereof |
| PEG | Anti-PEG antibody or antigen binding fragment thereof |
| Cyclodextrin | Anti-cyclodextrin or antigen binding fragment thereof |
| Any hapten | Immunoglobin or antigen binding fragment thereof |
| Digitoxin | Anti-digitoxin antibody or antigen binding fragment thereof |
| Digoxigenin | Anti-digoxigenin antibody or antigen binding fragment thereof |
| Molecular imprint template | Molecular imprint |
| Dinitrophenyl | Immunoglobin or antigen binding fragment thereof |
| Nitrophenyl | Immunoglobin or antigen binding fragment thereof |

H. Nucleic Acid Amplification Methods

Additional nucleic acid amplification methods may be employed by amplifying the docking strains described herein. Thus, methods and constructs herein may benefit from both antigen:antigen-specific binding partner amplification, but they may also benefit from nucleic acid amplification.

In nucleic acid amplification methods, an oligonucleotide (such as a docking strand) bound (directly or indirectly) to the target-recognizing moiety is amplified using an amplifier strand (in some instances a circular DNA template), followed by extension of the docking strand by a DNA polymerase to create a concatemeric repeat of the reverse complement of the amplifier strand (i.e. an amplified strand or rolling circle amplification (RCA) product).

Figure 1B:
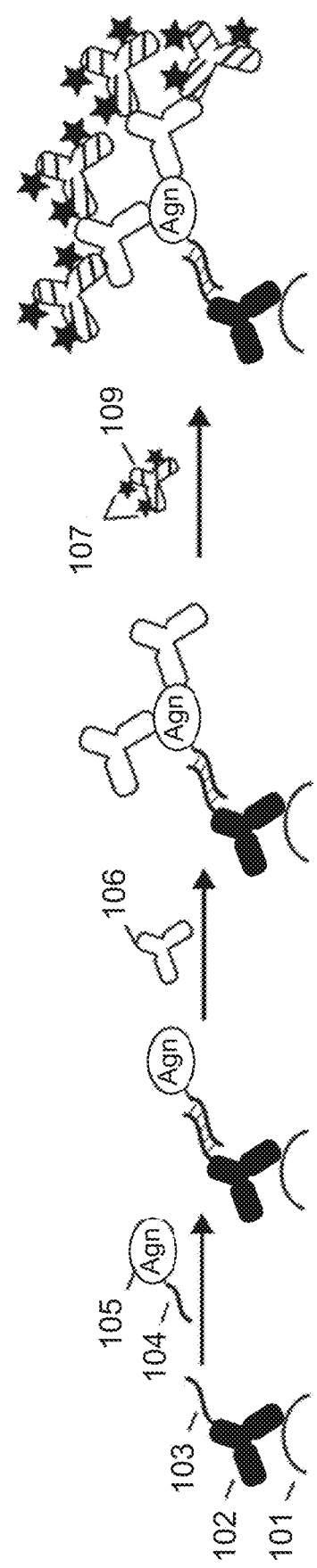
Figure 1C:
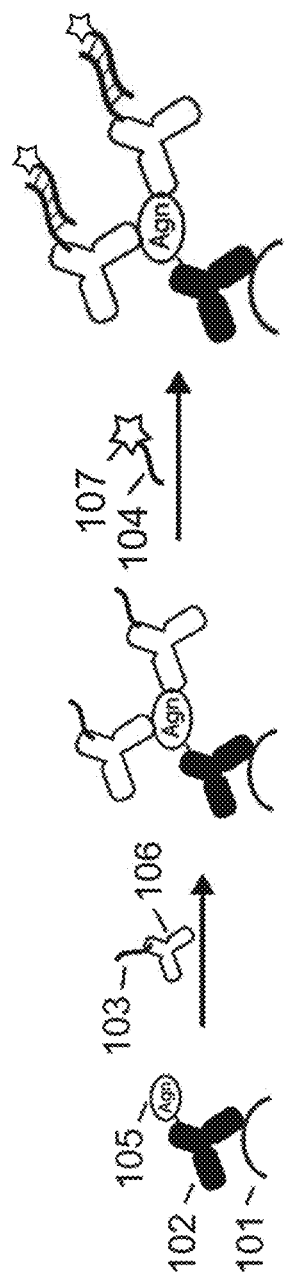
Figure 1D:
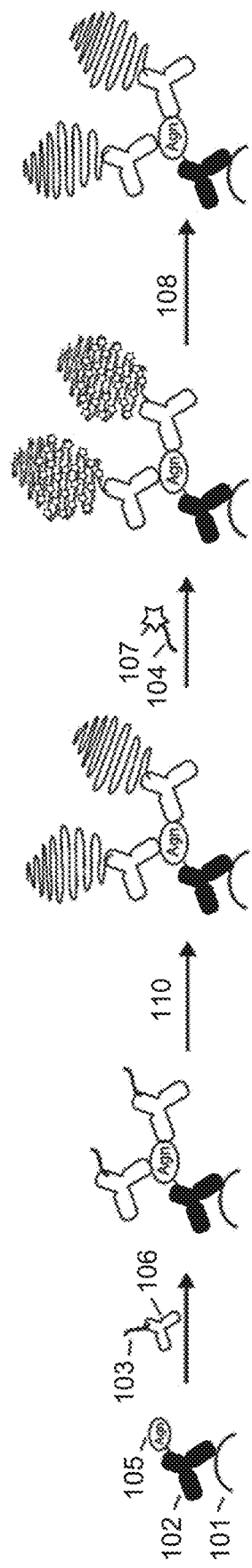
Figure 1E:
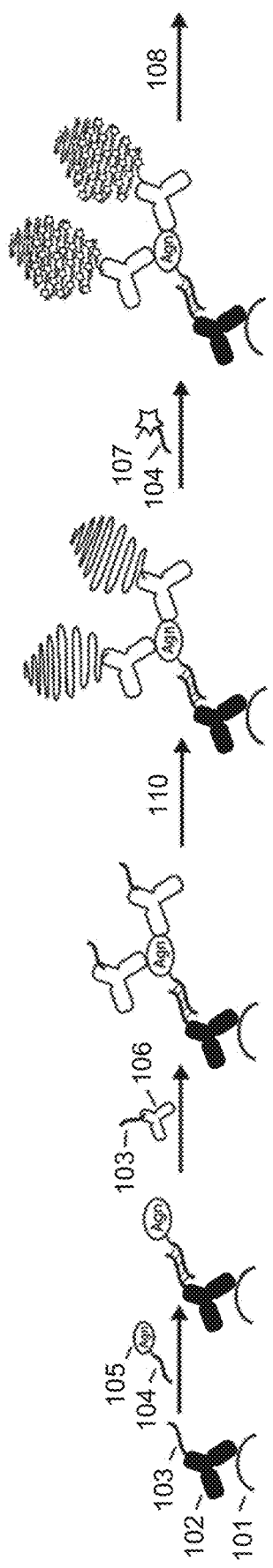
Figure 1F:
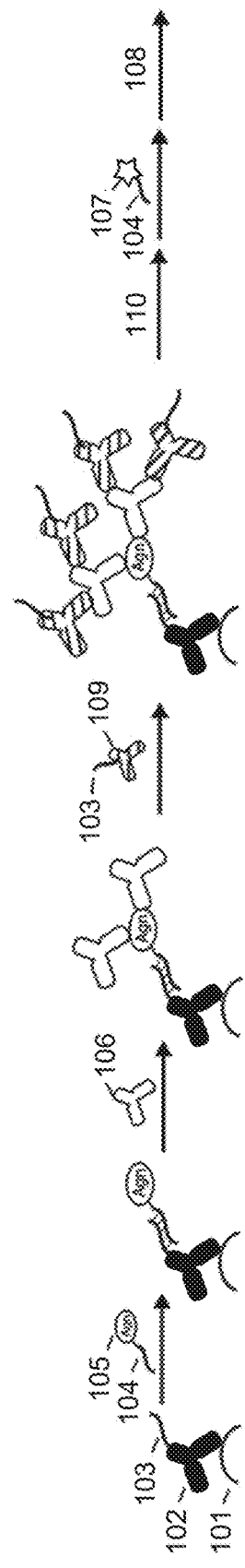

The use of nucleic acid amplification, such as RCA, is shown in FIGS. 1D-1F. The docking strand may, in fact, serve as a primer molecule for a polymerization or dendrimerization reaction. One example of such polymerization reactions is RCA where the primer of the RCA is linked (directly or indirectly, for example see FIGS. 1D and 1E) to the target-recognizing molecule and is converted to a long repetitive single-stranded DNA. Fluorescent molecules can be either directly incorporated into the RCA product via fluorescent-labeled nucleotides or be bound to the RCA product as a part of a fluorescent-labeled oligonucleotide that is designed to hybridize to the RCA product. Other examples of such polymerization or dendrimerization reactions include branched DNA toehold-based strand displacement (Schweller et al. PMCID: PMC3517005), hybridization chain reaction (HCR) (Dirks et al., 2014, PMID: 15492210, 24712299) and a similar DNA hairpin-based dendrimerization reaction (Yin et al., 2008, PMID 18202654), which here we call HDR. Other hairpin-based concatemerization methods may be used.

One may use RCA, HCR or HDR to generate a polymeric or dendrimeric product from the primer molecule linked to the antibody. In some embodiments, the product may contain many (e.g., greater than 2, 5, 10, 15, 20, 25, 50, 100, etc.) copies of single-stranded DNA domains that can serve as the docking strand and thus be recognized by oligonucleotides serving as the imager strand. Such DNA domains may be long enough (e.g. 7, 8, 9, 10, 11, 12, 13, 14, 15, 20, or more nucleotides long, or be able to bind its complementary strand with Kd<1 nM at imaging condition). For RCA, this is achieved regularly. For HCR and HDR, if necessary one can include, at the loop or tail of the substrate hairpin, DNA domains that do not participate in the strand-displacement cascades but constitute part or the entirety of the imager strand-binding site. In some embodiments, signal amplification involves linking (covalently or non-covalently) the target-recognizing molecule to a docking strand that serves as a primer molecule of a polymerization or dendrimerization reaction.

1. Rolling Circle Amplification

In rolling circle amplification, the docking strand that serves as a primer of the RCA is linked (directly or indirectly) to the target-recognizing molecule and is converted to a long repetitive single-stranded DNA. Fluorescent molecules can be either directly incorporated into the RCA product via fluorescent-labeled nucleotides or be bound to the RCA product as a part of a fluorescent-labeled oligonucleotide that is designed to hybridize to the RCA product.

In some embodiments, imager strands may be hybridized to the RCA product (e.g. the concatemeric repeat of the reverse complement of the amplifier strand) linked (directly or indirectly) to the target-recognizing moiety) during the RCA reaction. In some embodiments, therefore, amplification occurs using rolling circle amplification, while in the presence of labeled imager strands having complementarity to the amplified strand. For example, a sample may be contacted with an oligonucleotide docking strand conjugated to a target-recognizing moiety that is either prehybridized to an amplifier strand or the amplifier strand may be hybridized in a later step. Then, all additional components for the RCA reaction may be added in one step including proteins (e.g. DNA polymerases, optionally BSA), nucleotides, buffer solution, salts, and imager strands. In some embodiments, a user may wish to prevent the imager strand from being amplified. This can be accomplished by several means, including, but not limited to employing a 3'-modified imager strand having a modification on the 3' end. For example, the 3' modification on the imager strand may include a label (such as a fluorophore), a modified base, a stop code or terminator, a 3'-O-modification, a dideoxy-C, a dideoxy-G, a dideoxy-A, a dideoxy-T, an inverted nucleotide, any modification that eliminates the presence of a 3' hydroxyl group, or a single-stranded extension of the 3' end that is not complimentary to the amplifier strand.

In addition to HCR and RCA, other examples of such polymerization or dendrimerization reactions include, but are not limited to, DNA hairpin-based dendrimerization reaction (HDR) (Yin et al., 2008, PMID 18202654), and toe-hold mediated strand displacement.

DNA strand displacement is a method for the isothermal and dynamic exchange of DNA complexes. Strand displacement can be designed and intentionally controlled based on an understanding of DNA hybridization interactions and thermodynamics and can be facilitated by introducing engineered handles which are known as "toehold domains." The ability to modulate binding interactions and exchange hybridization partners gives rise to a series of potential signal amplification applications.

The amplification of multiple targets can be carried out sequentially. Alternatively, the amplification of multiple targets can be carried out simultaneously. Imaging steps can be carried out between rounds of amplification or following all rounds of amplification.

Multiple types of signal amplification can even be used in combination. For example, Gusev et al reported combining rolling circle amplification and HRP-based signal amplification (PMID: 11438455).

2. Nonlinear Amplification

An alternative method of RCA involves the use of a nonlinear amplifier or template strand, wherein an oligonucleotide (such as a docking strand) bound (directly or indirectly) to the target-recognizing moiety is hybridized to a circular DNA template (amplifier strand), followed by extension of the docking strand by a DNA polymerase to create a concatemeric repeat of the reverse complement of the amplifier strand (i.e. an amplified strand or RCA product). The hybridization of the amplifier strand to the oligonucleotide conjugated target-recognizing moiety may occur before (preassembly or prehybridization) or after the oligonucleotide conjugated target-recognizing moiety contacts the sample.

A nonlinear DNA template could be employed for signal amplification as a circular amplification strand. A circular oligo, with complementarity to a docking strand, can be generated separately from the amplification method. For example, ex situ ligation could be performed on a template DNA strand to form a circular strand of DNA. A circular strand could be hybridized to a docking strand that is attached to a target-specific binding partner before contacting the sample. Alternatively, the target-specific binding partner could first be used to stain the sample, and then subsequently the circular strand could be introduced to the sample to hybridize with the docking strand on the target-specific binding partner. Following the formation of a complex wherein a circular strand is attached to a docking strand that is linked to a target-specific binding partner, rolling circle amplification (RCA) could be carried out. This method offers certain advantages as it can be used to circumvent issues with inefficient in situ ligation steps.

In some embodiments, a polymerase may be used for RCA. In some instances, the labeled imager strands are linear strands. In some instances, the nonlinear amplifier strands are circular strands. In some instances, the nonlinear amplifier strands are branched strands. In some instances, the nonlinear amplifier strand becomes circular after ligation.

In some embodiments, amplification products may comprise a geometric shape, such as a triangle, quadrilateral, pentagon, hexagon, and the like.

I. Optical Labels

Various optical labels, also known as observable moieties, may be employed for signaling purposes. The optical labels may be bound to the antigen-specific binding partner (see FIG. 1A). The optical labels may be bound to the secondary binding partner that specifically binds to the antigen-specific binding partner (see FIG. 1B). The optical label may be bound to an imager strand (see FIGS. 1C, 1D, and 1E). The optical label may be bound to a nucleotide and incorporated into a nucleic acid amplification reaction (similar to FIGS. 1D and 1E but without an imager strand). Thus, the optical labels may be bound directly or indirectly to the antigen-specific binding partner.

In some embodiments, any observable moiety may be employed and, in some embodiments, the moiety is optically observable. The moiety may be signal absorbing or signal emitting. Of signal emitting molecules, molecules that fluoresce may be used, such as organic small molecules, including, but not limited to fluorophores, such as, but not limited to, fluorescein, Rhodamine, cyanine dyes, Alexa dyes, DyLight dyes, Atto dyes, etc.

In some embodiments, organic polymers, such as p-dots may be employed. In some embodiments, the observable moiety may be a biological molecule, including but not limited to a fluorescent protein or fluorescent nucleic acid (including fluorescent RNAs including Spinach and its derivatives). In some embodiments, the observable moiety may be an inorganic moiety including Q-dots. In some embodiments, the observable moiety may be a moiety that operates through scattering, either elastic or inelastic scattering, such as nanoparticles and Surface Enhanced Raman Spectroscopy (SERS) reporters (e.g., 4-Mercaptobenzoic acid, 2,7-mercapto-4-methylcoumarin). In some embodiments, the observable moiety may be chemiluminescence/electrochemiluminescence emitters such as ruthenium complexes and luciferases. The observable moiety may generate an optical signal, an electromagnetic signal (across the entire electromagnetic spectrum), atomic/molecular mass (e.g. detectable by mass spectrometry), tangible mass (e.g., detectable by atomic force microscope), current or voltage.

In some embodiments, the antigen-specific binding partner with the optical label may have multiple labels or observable moieties. For example, if the antigen-specific binding partner is streptavidin, it may be able to carry at least 5 or 6 fluorophores. Depending on the degree of signal desired, larger antigen-specific binding partners may be used to generate additional signaling capacity.

J. Sample

The reagents and techniques described herein may be useful for interrogating a plurality of different samples. In some instances, the sample is a cell, cell lysate, tissue, tissue lysate, a bodily fluid and/or a whole organism.

EXAMPLES

Figures 2A, 2B, 2C, 2D:
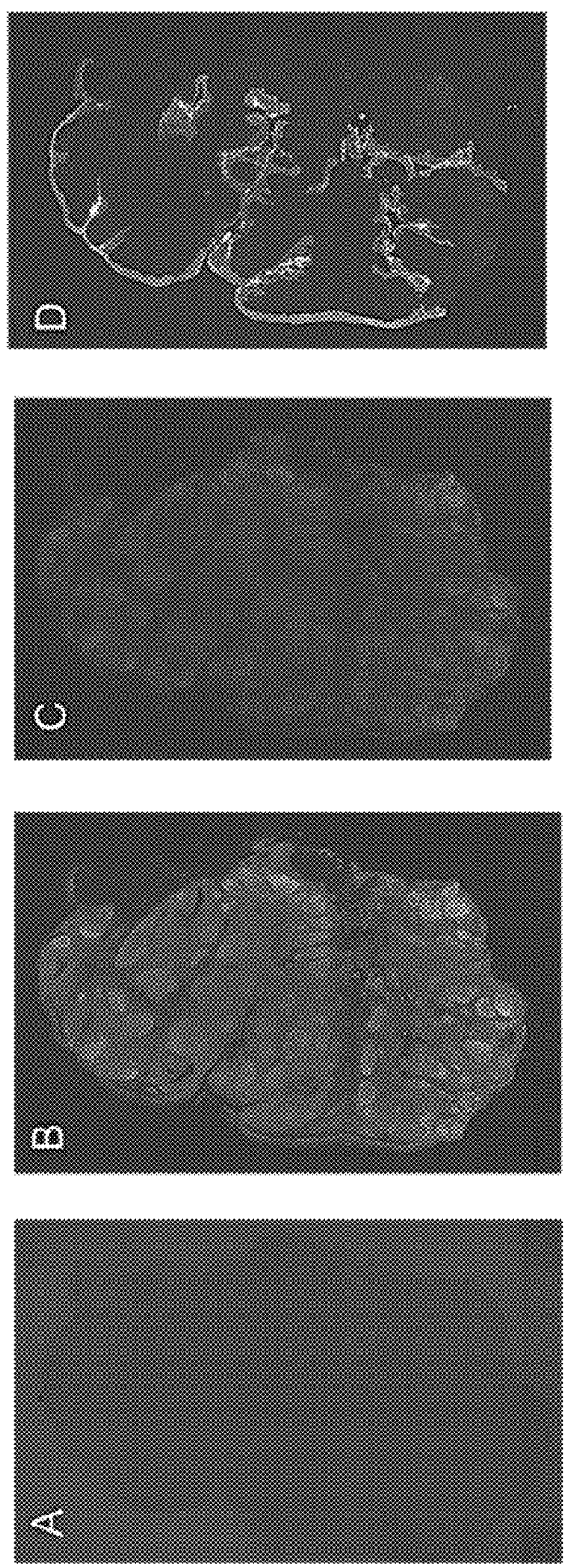
FIGS. 2A-D show data demonstrating the DNA Antigen Exchange results for a 2-plex assay on tonsil tissue using biotinylated imager strands and dye-labeled streptavidin.

Example 1. DNA-Antigen Exchange with Biotin Antigen and Dye-Labeled Streptavidin in Tissue Formalin-fixed paraffin-embedded (FFPE) tonsil tissue sections were dewaxed and antigen-retrieved using PT buffer (pH 6) in a Lab Vision PT-module. Tissue sections were blocked in 3% BSA and 0.2% Triton-X 100 for 1.5 hours, then rinsed in 1×PBS. Tissue sections were stained with mouse anti-cytokeratin and rabbit anti-Ki67 primary antibodies overnight at 4C in a humidity chamber. Tissue sections were then washed with 1×PBS and stained for 1.5 hours at room temperature with a goat anti-mouse secondary antibody conjugated to a DNA docking strand (D1) and a goat anti-rabbit antibody conjugated to a different DNA docking strand (D2). Tissue sections were washed again in 1×PBS and stained for DAPI. A fluorescence microscope was used to image the tissue section in the DAPI and Cy5 channels to serve as a blank. (See FIG. 2A)

An imager strand (I1-bio), comprising a biotinylated DNA strand hybridized to a DNA strand that includes a domain complementary to a docking strand D1, was added to the prepared tissue section and allowed to hybridize for 25 minutes at room temperature. Sections were washed to remove unbound I1-bio. Then, a solution of Cy5 labeled streptavidin (SA-Cy5) was added and allowed to incubate for 30 minutes at room temperature. The tissue was washed in 1×PBS with 0.1% Tween-20. After washing, fluorescence images were captured in the DAPI and Cy5 channels using a 10× objective. (See FIG. 2B)

The imager strand I1-bio was then removed by applying 10 units of USER enzyme to the tissue sections for 15 minutes at room temperature, washing with 1×PBS. A fluorescence microscope was used to confirm the complete removal of fluorescent signal in the Cy5 channel. (See FIG. 2C).

An imager strand (I2-bio), comprising a biotinylated DNA strand hybridized to a DNA strand that includes a domain complementary to a docking strand D2, was added to the prepared tissue section and allowed to hybridize for 25 minutes at room temperature. Sections were washed to remove unbound I2-bio. Then, a solution of Cy5 labeled streptavidin (SA-Cy5) was added and allowed to incubate for 30 minutes at room temperature. The tissue was washed in 1×PBS with 0.1% Tween-20. After washing, fluorescence images were captured in the DAPI and Cy5 channels using a 10× objective. (See FIG. 2D).

Example 2. DNA-Antigen Exchange with HRP Antigen and Dye-Labeled Anti-HRP Antibody Formalin-fixed paraffin-embedded (FFPE) tonsil tissue sections were dewaxed and antigen-retrieved using PT buffer (pH 6) in a Lab Vision PT-module. Tissue sections were blocked in 3% BSA and 0.2% Triton-X 100 for 1.5 hours, then rinsed in 1×PBS. Tissue sections were stained with mouse anti-cytokeratin and rabbit anti-Ki67 primary antibodies overnight at 4C in a humidity chamber. Tissue sections were then washed with 1×PBS and stained for 1.5 hours at room temperature with a goat anti-mouse secondary antibody conjugated to a DNA docking strand (D1) and a goat anti-rabbit antibody conjugated to a different DNA docking strand (D2). Tissue sections were washed again in 1×PBS and stained for DAPI. A fluorescence microscope was used to image the tissue section in the DAPI and Cy5 channels to serve as a blank.

Figure 3B:
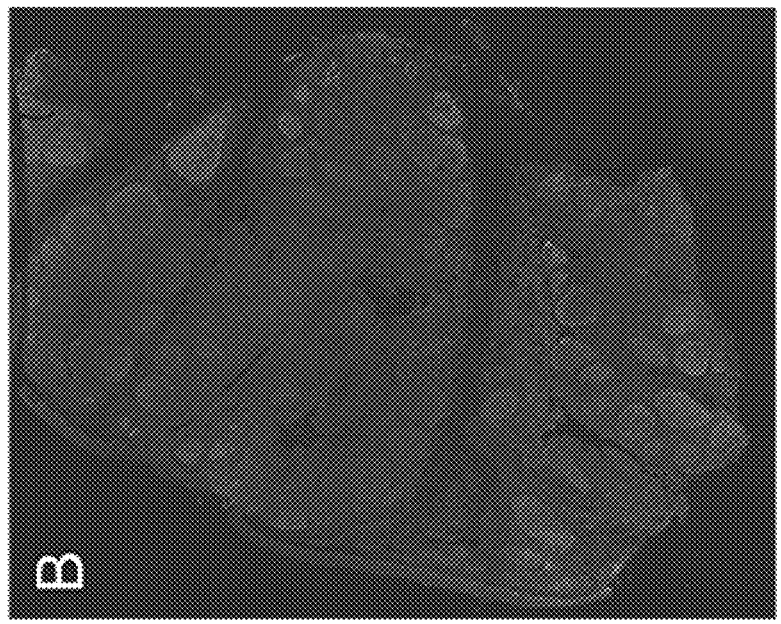
FIGS. 3A-B illustrate amplification using DNA Antigen Exchange with HRP-labeled imager strands and dye-labeled anti-HRP antibodies (FIG. 3A) compared to non-amplified image with fluorophore-labeled imager strand (FIG. 3B). Brightness scale set from 0-3000 for both images.
Figure 3A:
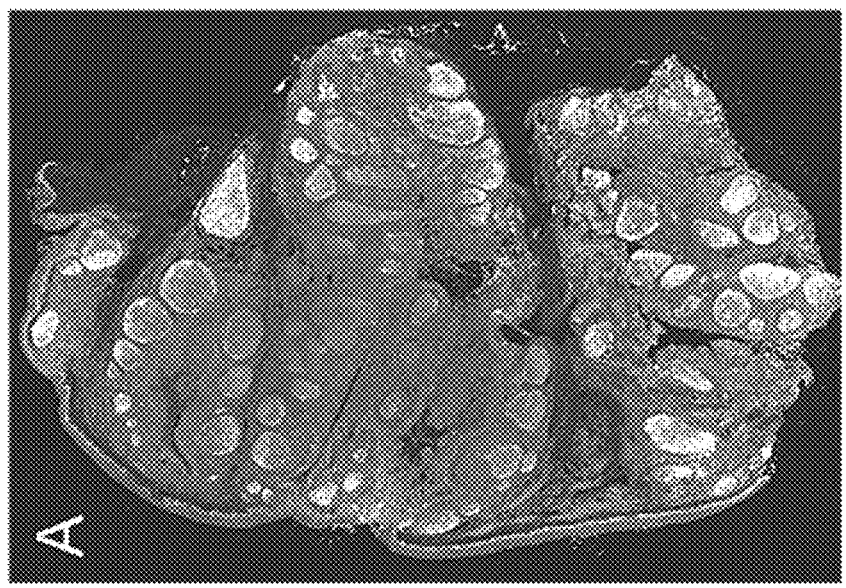

An imager strand (I2-HRP), comprising an HRP-conjugated DNA strand hybridized to a DNA strand that includes a domain complementary to a docking strand D2, was added to the prepared tissue section and allowed to hybridize for 25 minutes at room temperature. Sections were washed to remove unbound I2-HRP. Then, the tissue section was stained with a goat anti-HRP antibody conjugated to Alexa- 647 for 1.5 hours at room temperature, protected from light. Unbound material was removed by washing in 1×PBS with 0.1% Tween-20. After washing, fluorescence images were captured in the DAPI and Cy5 channels using a 10× objective. (See FIG. 3).

Figure 4:
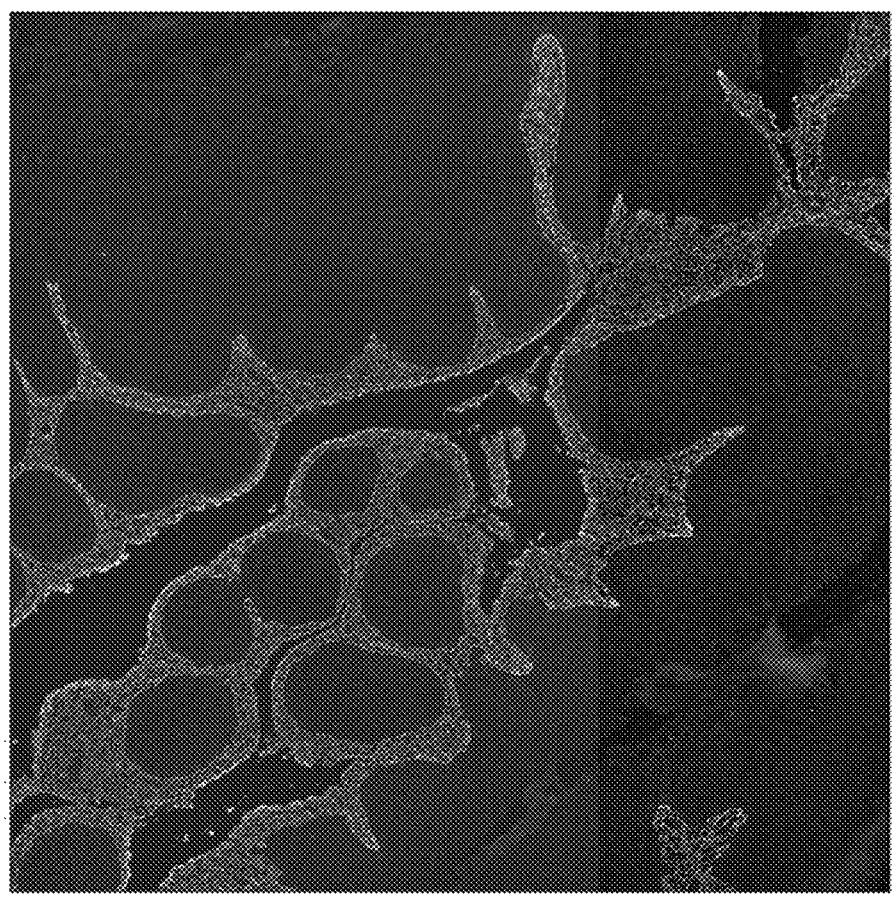
FIG. 4 shows data demonstrating DNA-antigen amplification on cytokeratin protein targets in FFPE tonsil tissue. Antigen-conjugated primary antibodies and DNA-conjugated anti-antigen antibodies were used to stain cytokeratin; rolling circle amplification was employed to increase the number of docking strands associated with the DNA-conjugated anti-antigen antibody; and fluorescently labeled imager strands were bound prior to imaging the sample.

Example 3. DNA-Antigen Exchange with Directly Labeled Antigen and DNA-Labeled Anti-Antigen Antibody Formalin-fixed paraffin-embedded (FFPE) tonsil tissue sections were dewaxed and antigen-retrieved using PT buffer (pH 9) in a Lab Vision PT-module. Tissue sections were blocked in 3% BSA and 0.2% Triton-X 100 for 1.5 hours, then rinsed in 1×PBS. Tissue sections were stained with mouse anti-cytokeratin primary antibody conjugated to dinitrophenyl (DNP) for 1 hour at room temperature, then washed to remove unbound primary antibody DNP conjugates. Tissue sections were then stained for 1.5 hours at room temperature with an anti-DNP KLH polyclonal antibody conjugated to a docking strand. Amplification of the docking strands was carried out using rolling circle amplification (RCA). Following the RCA reaction, imager strands with complementarity to the docking strands and labeled with Cy5.5 fluorophores were added and allowed to incubate for 25 minutes at room temperature to bind to the sample. Unbound imager strands were washed away and the sample was imaged with a fluorescent microscope (FIG. 4).

Example 4: Certain Embodiments

Item A. In some embodiments, the antigen-specific binding partners and antigen-bound imager strands are added stepwise in the method herein. Namely, a method comprising:
(1) contacting a sample being tested for the presence of one or more targets with one or more target-specific binding partners, wherein each target-specific binding partner is linked to a docking strand, and wherein target-specific binding partners of different specificity are linked to different docking strands,
(2) optionally removing unbound target-specific binding partners,
(3) contacting the sample with antigen-bound imager strands having complementarity to a docking strand, directly or indirectly,
(4) optionally removing unbound antigen-bound imager strands,
(5) contacting the sample with labeled antigen-specific binding partner, wherein each antigen-specific binding partner is linked to one or more optical labels, and wherein antigen-specific binding partners of different specificity are linked to distinct optical labels,
(6) optionally removing unbound antigen-specific binding partners,
(7) imaging the sample to detect bound labeled antigen-specific binding partners,
(8) optionally removing/extinguishing signal from the optical labels (i.e., signal termination), and
(9) optionally repeating steps (1)-(9), or any subset thereof (such as (1)-(8) or other subset, keeping in mind some steps may not be repeated, especially the signal termination step).

Item B. In some embodiments, the antigen-specific binding partners and antigen-bound imager strands are premixed before including them in the method herein. Namely, a method comprising:
(1) contacting a sample being tested for the presence of one or more targets with one or more target-specific binding partners, wherein each target-specific binding partner is linked to a docking strand, and wherein target-specific binding partners of different specificity are linked to different docking strands,
(2) optionally removing unbound target-specific binding partners,
(3) contacting the sample with labeled antigen-specific binding partners, wherein each antigen-specific binding partner is linked to one or more optical labels, wherein antigen-specific binding partners of different specificity are linked to distinct optical labels, and wherein the labeled antigen-specific binding partners are bound to antigen-bound imager strands having complementarity to a docking strand, directly or indirectly,
(4) optionally removing unbound labeled antigen-specific binding partners and antigen-bound imager strands,
(5) imaging the sample to detect bound labeled antigen-specific binding partners,
(6) optionally removing/extinguishing signal from the optical labels (i.e., signal termination), and
(7) optionally repeating steps (1)-(7), or any subset thereof (such as (1)-(6) or other subset, keeping in mind some steps may not be repeated, especially the signal termination step).

Item C. A method comprising:
(1) contacting a sample being tested for the presence of one or more targets with one or more target-specific binding partners, wherein each target-specific binding partner is linked to a docking strand, and wherein target-specific binding partners of different specificity are linked to different docking strands,
(2) optionally removing unbound target-specific binding partners,
(3) contacting the sample with labeled imager strands having complementarity to a docking strand, directly or indirectly,
(4) optionally removing unbound labeled imager strands,
(5) imaging the sample to detect bound labeled imager strands,
(6) removing bound labeled imager strands,
(7) increasing the observable signal by contacting the sample with antigen-bound imager strands having complementarity to a docking strand, directly or indirectly,
(8) optionally removing unbound antigen-bound imager strands,
(9) contacting the sample with labeled antigen-specific binding partner, wherein each antigen-specific binding partner is linked to one or more optical labels, and wherein antigen-specific binding partners of different specificity are linked to distinct optical labels,
(10) optionally removing unbound antigen-specific binding partners,
(11) imaging the sample to detect bound labeled antigen-specific binding partners,
(12) optionally removing/extinguishing signal from the optical labels (i.e., signal termination), and
(13) optionally repeating steps (1)-(13), or any subset thereof (such as (1)-(12) or other subset, keeping in mind some steps may not be repeated, especially the signal termination step).

Example 5: Additional Embodiments

The following numbered items provide additional support for and descriptions of the embodiments herein.

Item 1. A method comprising:
(1) contacting a sample being tested for the presence of one or more targets with one or more target-specific binding partners, wherein each target-specific binding partner is linked to a docking strand, and wherein target-specific binding partners of different specificity are linked to different docking strands,
(2) optionally removing unbound target-specific binding partners,
(3) contacting the sample with antigen-bound imager strands and antigen-specific binding partners linked (directly or indirectly) to optical labels,
   wherein the antigen-bound imager strands have complementarity to a docking strand, directly or indirectly, and
   wherein each antigen-specific binding partner is linked to one or more optical labels, and wherein antigen-specific binding partners of different specificity are linked to distinct optical labels,
(4) optionally removing unbound antigen-bound imager strands and/or antigen-specific binding partners,
(5) imaging the sample to detect bound labeled antigen-specific binding partners,
(6) optionally removing/extinguishing signal from the optical labels (i.e., signal termination), and
(7) optionally repeating steps (1)-(8), or any subset thereof (such as (1)-(6) or other subset, keeping in mind some steps may not be repeated, especially the signal termination step).

Item 2. A method comprising:
(1) contacting a sample being tested for the presence of one or more targets with one or more target-specific binding partners, wherein each target-specific binding partner is linked to an antigen, and wherein target-specific binding partners of different specificity are linked to different antigens,
(2) optionally removing unbound target-specific binding partners,
(3) contacting the sample with antigen-specific binding partners linked to docking strands, wherein different antigen-specific binding partners are linked to different docking strands,
(4) optionally removing unbound antigen-specific binding partners linked to docking strands;
(5) adding imager strands;
   wherein the imager strands have complementarity to a docking strand, directly or indirectly, and
   wherein each imager strand is linked (directly or indirectly) to one or more optical labels, and wherein imager strands of different specificity are linked to distinct optical labels,
(6) optionally removing unbound imager strands,
(7) imaging the sample to detect bound labeled antigen-specific binding partners,
(8) optionally removing/extinguishing signal from the optical labels (i.e., signal termination), and
(9) optionally repeating steps (1)-(8), or any subset thereof (such as (1)-(7) or other subset, keeping in mind some steps may not be repeated, especially the signal termination step).

Item 3. A method comprising:
(1) contacting a sample being tested for the presence of one or more targets with one or more target-specific binding partners, wherein each target-specific binding partner is linked to a first docking strand, and wherein target-specific binding partners of different specificity are linked to different docking strands,
(2) optionally removing unbound target-specific binding partners,
(3) contacting the sample with antigen-bound imager strands and antigen-specific binding partners,
   wherein the antigen-bound imager strands have complementarity to a docking strand, directly or indirectly, and
   wherein each antigen-specific binding partner is linked to at least one second docking strand;
(4) optionally removing unbound antigen-bound imager strands and/or antigen-specific binding partners,
(5) increasing the number of second docking strand strands by a DNA amplification reaction and labeling of the second docking strands using an optical label,
(6) imaging the sample to detect bound labeled antigen-specific binding partners,
(7) optionally extinguishing the signal from the optical label (i.e., signal termination), and
(8) optionally repeating steps (1)-(8), or any subset thereof (such as (1)-(7) or other subset, keeping in mind some steps may not be repeated, especially the signal termination step).

Item 4. The method of item 3, wherein the first docking strand and the second docking strand have a different sequence.

Item 5. The method of item 3, wherein the first docking strand and the second docking strand have the same sequence.

Item 6. A method comprising:
(1) contacting a sample being tested for the presence of one or more targets with one or more target-specific binding partners, wherein each target-specific binding partner is linked to an antigen, and wherein target-specific binding partners of different specificity are linked to different antigens,
(2) optionally removing unbound target-specific binding partners,
(3) contacting the sample with antigen-specific binding partners linked docking strands, wherein different antigen-specific binding partners are linked to different docking strands,
(4) optionally removing unbound antigen-specific binding partners linked to docking strands;
(5) increasing the number of docking strands by a DNA amplification reaction and labeling of the docking strands using an optical label,
(6) imaging the sample to detect bound labeled antigen-specific binding partners,
(7) optionally extinguishing the signal from the optical label (i.e., signal termination), and
(8) optionally repeating steps (1)-(8), or any subset thereof (such as (1)-(7) or other subset, keeping in mind some steps may not be repeated, especially the signal termination step).

Item 7. The method of any one of items 3-6, wherein the docking strands are directly labeled using labeled nucleotides in the DNA amplification reaction.

Item 8. The method of item 7, wherein the labeled nucleotides are fluorescently-labeled nucleotides.

Item 9. The method of any one of items 3-6, wherein the docking strands are labeled using a labeled nucleic acid that binds to the docking strand.

Item 10. The method of any one of items 3-9, wherein the DNA amplification reaction comprises rolling circle amplification.

Item 11. The method of items 3-9, wherein the DNA amplification reaction comprises hybridization chain reaction.

Item 12. The method of items 3-9, wherein the DNA amplification reaction comprises hairpin-based concatemerization (including dendrimerization) reaction.

Item 13. The method of any one of items 1, 3-5, or 7-12, wherein steps (3) and (4) together comprise:
a. first contacting the sample with antigen-bound imager strands,
b. second optionally removing unbound antigen-bound imager strands,
c. third contacting the sample with labeled antigen-specific binding partner, and
d. fourth optionally removing unbound antigen-specific binding partners.

Item 14. The method of any one of items 1, 3-5, or 7-13, wherein between steps (2) and (3), the method comprises:
a. contacting the sample with labeled imager strands having complementarity to a docking strand, directly or indirectly,
b. optionally removing unbound labeled imager strands,
c. imaging the sample to detect bound labeled imager strands, and
d. removing the bound labeled imager strands from the docking strands.

Item 15. The method of any one of items 1, 3-5, or 7-14, wherein step (3) comprises contacting the sample with antigen-specific binding partners, wherein the antigen-specific binding partners are bound to antigen-bound imager strands.

Item 16. The method of any one of items 1-15, wherein the method includes removing antigen-bound imager strands not bound to docking strands.

Item 17. The method of any one of items 1, 3-5, 7-12, or 14-16, wherein the method includes removing antigen-specific binding partners not bound to antigen-bound imager strands.

Item 18. The method of any one of items 1-19, wherein the target-specific binding partner comprises an antibody or antigen-binding fragment thereof.

Item 19. The method of any one of items 1-18, wherein the target-specific binding partner comprises:
a. a known binding partner of a target molecule or a variant of such binding partner,
b. any binding partner of the target molecule engineered via directed evolution (e.g., peptides and aptamers), or
c. any molecule that selectively forms at least one covalent bond with a target (e.g., a suicide substrate of an enzyme of interest).

Item 20. The method of any one of items 1-19, wherein the docking strand is a nucleic acid strand.

Item 21. The method of any one of items 1-20, wherein the imager strand is a nucleic acid strand.

Item 22. The method of any one of items 1, 3-5, 7-12, 14-16, or 18-21, wherein the antigen of the antigen-bound imager strand comprises HRP.

Item 23. The method of any one of items 1-22, wherein the antigen-specific binding partner comprises an anti-HRP antibody or antigen binding fragment thereof.

Item 24. The method of any one of items 1, 3-5, 7-12, 14-16, 18-21, or 23, wherein the antigen of the antigen-bound imager strands comprises biotin.

Item 25. The method of any one of items 1-24, wherein the antigen-specific binding partner comprises streptavidin.

Item 26. The method of any one of items 1, 3-5, 7-12, 14-16, 18-21, 23, or 25, wherein the antigen-specific binding partner comprises an antibody or antigen binding fragment thereof that specifically binds the antigen of the antigen-bound imager strand.

Item 27. The method of any one of items 1, 3-5, 7-12, 14-16, 18-21, 23, or 25, wherein the antigen of the antigen-bound imager strand and the antigen-specific binding partner are both antibodies or antigen binding fragments thereof and the antigen-specific binding partner antibody or antigen binding fragment thereof binds to the antigen antibody or antigen binding fragment thereof of the antigen-bound imager strand.

Item 28. The method of any one of items 1-27, wherein the optical label comprises a signal-emitting molecule.

Item 29. The method of any one of items 1-38, wherein the optical label comprises a signal-absorbing molecule.

Item 30. The method of any one of items 1-29, wherein the sample is a cell, cell lysate, tissue, tissue lysate, a bodily fluid and/or a whole organism.

Item 31. The method of any one of items 1-30, wherein secondary binding partners linked to optical labels are introduced, wherein the secondary binding partners specifically bind the antigen-specific binding partners, either directly or indirectly.

Item 32. The method of any one of items 1, 3-5, 7-12, 14-16, 18-21, 23, 25, or 28-31, wherein secondary binding partners linked to optical labels are introduced, wherein the secondary binding partners specifically bind the antigen-specific binding partners, either directly or indirectly, and wherein the secondary binding partners and the antigen of the antigen-bound imager strands each comprise the same antigen.

Item 33. The method of any one of items 31-32, wherein the antigen and the secondary binding partner each comprise biotin.

Item 34. The method of any one of items 31-33, wherein the antigen-specific binding partner comprises streptavidin.

Item 35. The method of any one of items 1, 3-5, 7-12, 14-16, 18-21, 23, 25, 28-31, or 33-34, wherein secondary binding partners linked to optical labels are introduced, wherein the secondary binding partners specifically bind the antigen-specific binding partners, either directly or indirectly, and wherein the secondary binding partners do not comprise the antigen of the antigen-bound imager strands.

Item 36. The method of any one of items 31-35, wherein the antigen-specific binding partners and the secondary binding partners both comprise an antibody or an antigen-binding fragment thereof.

Item 37. The method of item 36, wherein the antigen-specific binding partner is a primary antibody or antigen-binding fragment thereof to the antigen and the secondary binding partner is a secondary antibody or antigen-binding fragment thereof.

Item 38. The method of any one of items 1-37, wherein multiple antigen-specific binding partners bind to a single antigen.

Item 39. The method of any one of items 1-38, wherein the antigen-specific binding partners comprise a polyclonal antibody.

Item 40. The method of any one items 44-41, wherein multiple types of antigen-specific binding partners are used.

Item 41. The method of item 40, wherein the multiple types of antigen-specific binding partners comprise more than one monoclonal antibody directed to different epitopes on the antigen.

Item 42. A composition comprising:
(1) a first binding partner-oligonucleotide conjugate comprising a binding partner linked to an oligonucleotide that comprises a docking domain;
(2) an antigen-bound oligonucleotide conjugate comprising an antigen linked to an oligonucleotide that comprises an imager domain, wherein the imager domain of (2) is complementary to the docking domain of (1); and
(3) a labeled antigen-specific binding partner comprising an optical label linked to an antigen-specific binding partner, wherein the antigen-specific binding partner of (3) specifically binds the antigen in (2).

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. Each number in the specification or claims may be considered modified by the term about. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method comprising:
(1) contacting a sample being tested for the presence of one or more targets with one or more target-specific binding partners, wherein each target-specific binding partner is linked to a docking strand, and wherein target-specific binding partners of different specificity are linked to different docking strands,
(2) optionally removing unbound target-specific binding partners,
(3) contacting the sample with antigen-bound imager strands and antigen-specific binding partners linked directly or indirectly to optical labels,
    wherein the antigen-bound imager strands have complementarity to a docking strand, directly or indirectly,
    wherein for at least some of the antigen-specific binding partners, the antigen-specific binding partner comprises an antibody or antigen binding fragment thereof that specifically binds the antigen of the antigen-bound imager strand, wherein the antigen is a protein or peptide, and
    wherein each antigen-specific binding partner is linked to one or more optical labels, and wherein antigen-specific binding partners of different specificity are linked to distinct optical labels,
(4) optionally removing unbound antigen-bound imager strands and/or antigen-specific binding partners,
(5) imaging the sample to detect bound labeled antigen-specific binding partners,
(6) optionally removing/extinguishing signal from the optical labels, and
(7) optionally repeating steps (1)-(6), or any subset thereof.

2. The method of claim 1, wherein steps (3) and (4) together comprise:
    a. first contacting the sample with antigen-bound imager strands,
    b. second optionally removing unbound antigen-bound imager strands,
    c. third contacting the sample with labeled antigen-specific binding partner, and
    d. fourth optionally removing unbound antigen-specific binding partners.

3. The method of claim 1, wherein between steps (2) and (3), the method comprises:
    a. contacting the sample with labeled imager strands having complementarity to a docking strand, directly or indirectly,
    b. optionally removing unbound labeled imager strands,
    c. imaging the sample to detect bound labeled imager strands, and
    d. removing the bound labeled imager strands from the docking strands.

4. The method of claim 1, wherein step (3) comprises contacting the sample with antigen-specific binding partners, wherein the antigen-specific binding partners are bound to antigen-bound imager strands.

5. The method of claim 1, wherein the method includes removing antigen-bound imager strands not bound to docking strands.

6. The method of claim 1, wherein the method includes removing antigen-specific binding partners not bound to antigen-bound imager strands.

7. The method of claim 1, wherein the target-specific binding partner comprises an antibody or antigen-binding fragment thereof.

8. The method of claim 1, wherein the target-specific binding partner comprises:
    a. a known binding partner of a target molecule or a variant of such binding partner,
    b. any binding partner of the target molecule engineered via directed evolution,
    c. any molecule that selectively forms at least one covalent bond with a target, or
    d. a peptide, an aptamer, or a suicide substrate of an enzyme of interest.

9. The method of claim 1, wherein the docking strand is a nucleic acid strand.

10. The method of claim 1, wherein the imager strand is a nucleic acid strand.

11. The method of claim 1, wherein the antigen of the antigen-bound imager strand comprises a first antibody or antigen binding fragment thereof and the antigen-specific binding partner comprises a second antibody or antigen binding fragment thereof and wherein the second antibody or antigen binding fragment thereof binds to the first antibody or antigen binding fragment thereof.

12. The method of claim 1, wherein secondary binding partners linked to optical labels are introduced, wherein the secondary binding partners specifically bind the antigen-specific binding partners, either directly or indirectly.

13. The method of claim 12, wherein the antigen-specific binding partners and the secondary binding partners both comprise an antibody or an antigen-binding fragment thereof.

14. The method of claim 13, wherein the antigen-specific binding partner is a primary antibody or antigen-binding fragment thereof to the antigen and the secondary binding partner is a secondary antibody or antigen-binding fragment thereof.

15. The method of claim 1, wherein secondary binding partners linked to optical labels are introduced, wherein the secondary binding partners specifically bind the antigen-specific binding partners, either directly or indirectly, and wherein the secondary binding partners and the antigen of the antigen-bound imager strands each comprise the same antigen.

16. The method of claim 1, wherein secondary binding partners linked to optical labels are introduced, wherein the secondary binding partners specifically bind the antigen-specific binding partners, either directly or indirectly, and wherein the secondary binding partners do not comprise the antigen of the antigen-bound imager strands.

17. The method of claim 1, wherein multiple antigen-specific binding partners bind to a single antigen.

18. The method of claim 1, wherein if the presence of more than one target is tested, multiple types of antigen-specific binding partners are used.

19. The method of claim 1, wherein the step of (6) removing/extinguishing signal from the optical labels is performed.

20. The method of claim 19, wherein the step (6) of removing/extinguishing the signal from the optical labels comprises: removing the antigen-bound imager strands from the docking strands; cleaving or degrading the imager strand and/or the docking strands; extinguishing the signal; extinguishing the signal using photobleaching; or removing the label from the moiety to which it has been attached.

* * * * *

UNITED STATES PATENT AND TRADEMARK OFFICE
CERTIFICATE OF CORRECTION

Page 1 of 1

PATENT NO. : 11,279,968 B2
APPLICATION NO. : 16/273581
DATED : March 22, 2022
INVENTOR(S) : Hennek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 211 days.

Signed and Sealed this
Twenty-ninth Day of November, 2022

Katherine Kelly Vidal
*Director of the United States Patent and Trademark Office*